United States Patent [19]

Nohda

[11] 4,449,798

[45] May 22, 1984

[54] EYE FUNDUS OBSERVATION APPARATUS

[75] Inventor: Masao Nohda, Yokosuka, Japan

[73] Assignee: Nippon Kogaku K.K., Tokyo, Japan

[21] Appl. No.: 353,910

[22] Filed: Mar. 2, 1982

[30] Foreign Application Priority Data

Mar. 27, 1981 [JP] Japan ................................. 56-44122

[51] Int. Cl.³ .......................... A61B 3/14; G03B 29/00
[52] U.S. Cl. ....................................... 351/207; 354/62
[58] Field of Search .......................... 351/207; 354/62

[56] References Cited

U.S. PATENT DOCUMENTS 4,146,310  3/1979  Kohayakawa et al. ................. 351/7

Primary Examiner—John K. Corbin
Assistant Examiner—Rodney B. Bovernick
Attorney, Agent, or Firm—Shapiro and Shapiro

[57] ABSTRACT

In an eye fundus observation apparatus wherein light-intercepting members for eliminating flare are provided at predetermined positions in an illumination optical path which are substantially conjugate with the cornea and the front surface of the crystalline lens of an eye being examined in a condition in which the apparatus is focused to the fundus of the eye, an observation opening is formed at a position substantially conjugate with a position between the cornea and the front surface of the crystalline lens of the eye whereat the magnification of the reflected image on the rear surface of the crystalline lens is approximately one-to-one magnification in a condition in which the apparatus is focused to the fundus of the eye.

6 Claims, 4 Drawing Figures

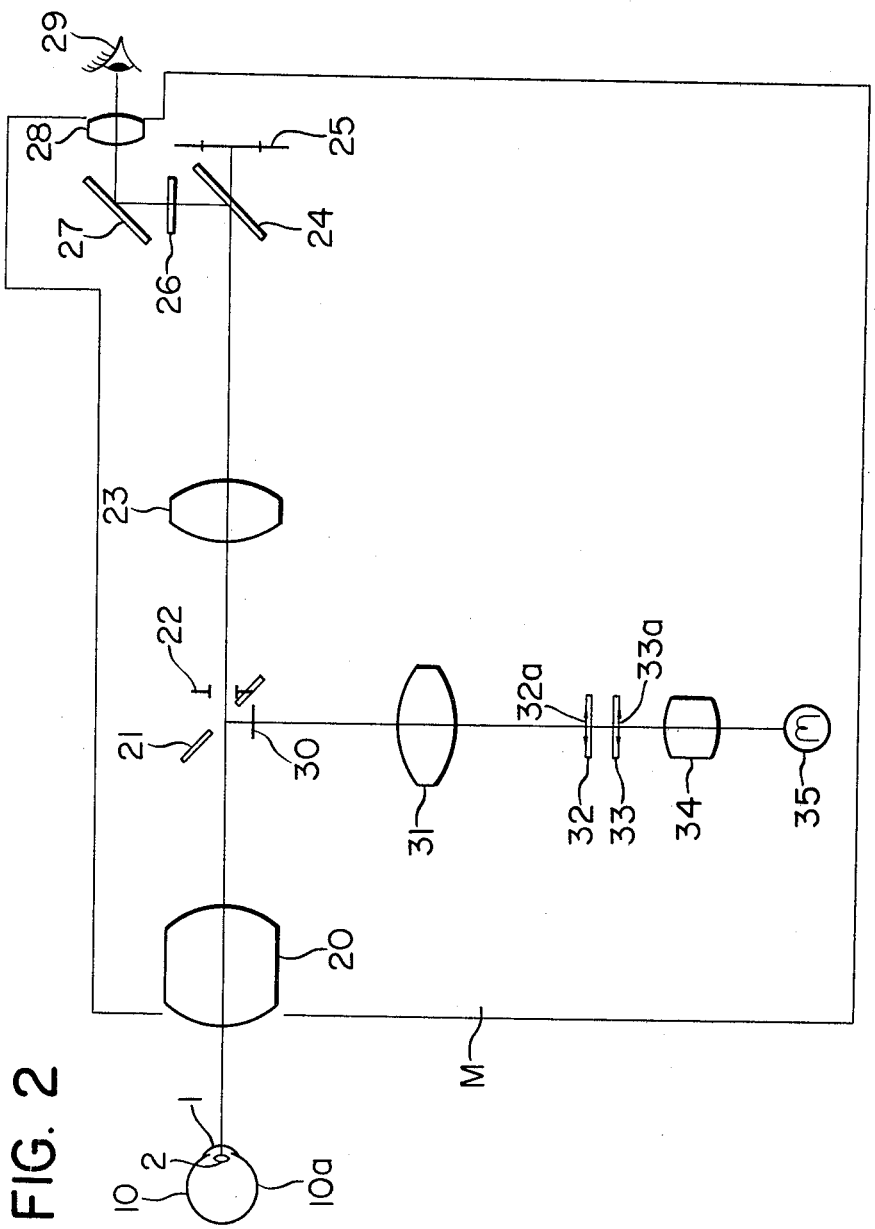

EYE FUNDUS OBSERVATION APPARATUS

BACKGROUND OF THE INVENTION

1. Field of the Invention

This invention relates to an eye fundus observation apparatus which can reduce the flare from the cornea or the crystalline lens of an eye to be examined created during the observation of the fundus of the eye and which enables even a small pupil to be observed at a wide angle of view, and more particularly to an eye fundus camera.

2. Description of the Prior Art

A sectional view of an eye as observed through a prior art apparatus of this type is shown in FIG. 1 of the accompanying drawings. A prior art apparatus is known in which light-intercepting members are provided at positions substantially conjugate with the cornea 1 and the front surface of the crystalline lines 2 of an eye to be examined in order that light-intercepting portions 10 and 20 for eliminating flare may be formed on the cornea 1 and the front surface of the crystalline lens 2 (which is also substantially coincident with the position of the pupil) as shown in FIG. 1. In this apparatus, an observation opening is formed at a position conjugate with the cornea 1 of the eye being examined and as a result, the light beam in the portion shown by hatching in the figure provides an observation light. In FIG. 1, it is the condition for eliminating the flare by the reflected light from the cornea 1 and the front surface of the crystalline lens 2 that the observation light beam does not swell out of the light-intercepting portions 10 and 20.

Accordingly, if an attempt is made to increase the observation angle of view, the light-intercepting portion 20 on the front surface of the crystalline lens 2 must be made large. However, the maximum light beam is limited by the iris 3 of the eye and therefore, if the light-intercepting portion 20 is made large, the quantity of illuminating light will be decreased. Also, where the iris 3 is small, the observation opening is shut out by the iris 3 and the fundus of the eye cannot be observed at a wide angle of view.

On the other hand, an eye fundus camera in which a light-intercepting portion is also formed on the rear surface of the crystalline lens 2 of the eye shown in FIG. 1 to further eliminate the reflection on the front surface of the crystalline lens 2 and the position conjugate with the observation opening is provided at the position of the pupil (the opening of the iris 3) is known as U.S. Pat. No. 4,146,310. In this camera, however, if the angle of view becomes wider, both of the light-intercepting portion on the cornea and the light-intercepting portion on the rear surface of the crystalline lens must be made larger and in that case, the quantity of illuminating light is decreased to about the same degree as in the case of FIG. 1 and thus, the inverse proportional relation between the increase in angle of view and the decrease in quantity of illuminating light is still left to be solved.

SUMMARY OF THE INVENTION

It is an object of the present invention to provide an eye fundus observation apparatus which can eliminate the flare from the cornea or the crystalline lens and enables the fundus of the eye to be observed brightly and efficiently at a wide angle of view.

According to the present invention, there can be provided an eye fundus observation apparatus in which light-intercepting members for eliminating flare are provided at predetermined positions in the illumination optical path which are substantially conjugate with the cornea and the front surface of the crystalline lens of an eye being examined when the apparatus is focused to the fundus of the eye and an observation opening is formed at a position conjugate with a position between the cornea and the front surface of the crystalline lens of the eye whereat the magnification of the reflected image on the rear surface of the crystalline lens is approximately one-to-one magnification, thereby eliminating the flare from the cornea or the crystalline lens and enabling the fundus of the eye to be observed brightly and efficiently at a wide angle of view.

The invention will become more fully apparent from the following detailed description thereof taken in conjunction with the accompanying drawings.

BRIEF DESCRIPTION OF THE DRAWINGS

FIG. 2 shows the optical system of an eye fundus camera which is an embodiment of the present invention.

DESCRIPTION OF THE PREFERRED EMBODIMENT

Figure 1:
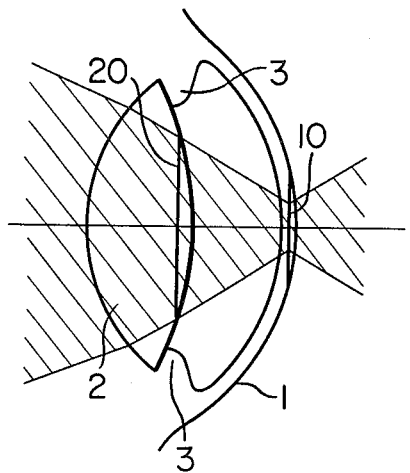
FIG. 1 is a sectional view of an eye as observed through an eye fundus observation apparatus according to the prior art.

The invention will hereinafter be described with respect to an embodiment shown in the drawings.

Figure 3:
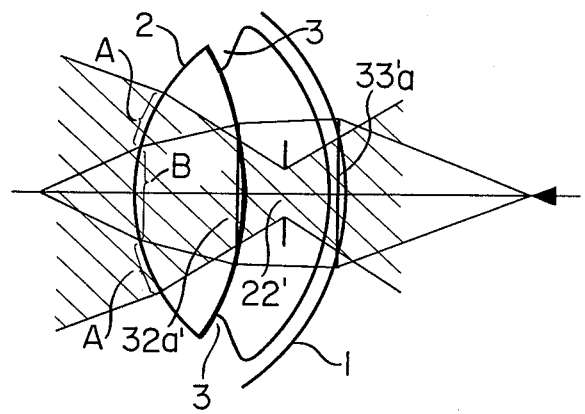
FIG. 3 illustrates the optical condition in the eye being examined when the eye fundus camera of FIG. 2 is used.

FIG. 2 shows the optical system of an eye fundus camera which is an embodiment of the present invention, and FIG. 3 shows the optical condition in an eye being examined when the eye fundus camera of FIG. 2 is used.

Figure 4:
FIG. 4 is a plan view of the light-intercepting member 32, 33 of FIG. 2.

In the eye fundus camera M of FIG. 2, reference numeral 20 designates an objective lens, reference nemeral 21 denotes an apertured reflecting mirror, reference numeral 22 designates an observation opening, reference numeral 23 denotes a phototaking lens, reference numeral 24 designates an optical path changing mirror, reference numeral 25 denotes a film surface, reference numeral 26 designates a focusing screen lying at a position optically equivalent to the film surface 25 with respect to the phototaking lens 23, reference numeral 27 denotes a mirror, reference numeral 28 designates an eyepiece for observing the focusing screen 24, reference numeral 30 designates a position optically equivalent to the observation opening 22 with respect to the objective lens 20, reference numeral 31 denotes a relay lens, and reference numerals 32 and 33 designate light-intercepting members having small circular light-intercepting portions 32a and 33a centered at an illumination optical axis, the light-intercepting members 32 and 33 being, for example, black spots provided on a transparent flat plate as shown in FIG. 4. The light-intercepting members 32 and 33 are disposed so that the portion between the light-intercepting members 32 and 33 becomes a position conjugate with the position 30 with respect to the relay lens 31. Reference numeral 34 designates a condenser lens and reference numeral 35 denotes a light source. Reference numeral 10 designates an eye to be examined, and reference numeral 29 denotes the eye of an examiner. As the light source 35, a light source for observation and a light source for phototaking may be used discretely as shown in U.S. Pat. No. 4,646,310. In that case, an infrared ray emitting light source can be used as the light source for observation.

The differences of this eye fundus camera from the prior art apparatus through which the observation as shown in FIG. 1 is effected are that in a condition in which the camera is focused to the fundus 10a of the eye 10 being examined, (a) the light-intercepting member 32 is disposed at a position substantially conjugate with the front surface of the crystalline lens 2 of the eye 10 by the relay lens 31 and the objective lens 20 and the light-intercepting member 33 is disposed at a position substantially conjugate with the cornea 1 of the eye 10 and (b) the observation opening 22 is provided at a position conjugate with a position between the cornea 1 and the crystalline lens 2 of the eye 10 whereat the magnification of the reflected image on the rear surface of the crystalline lens 2 is approximately one-to-one magnification. With such a construction, the light emitted from the light source 35 passes through the condenser lens 34, whereafter it illuminates the light-intercepting members 33 and 32. The light beam which has passed through the ring-like opening around the light-intercepting members 33, 32 passes through the relay lens 31, the apertured reflecting mirror 21 and the objective lens 20 to illuminate the fundus 10a of the eye 10. At this time, the light-intercepting portions 33a and 32a of the light-intercepting members 33 and 32 are imaged on the cornea 1 and the front surface of the crystalline lens 2 of the eye 10. The reflected light from the eye fundus 10a again passes through the objective lens 20, the apertured reflecting mirror 21, the phototaking lens 23 and the mirror 24 to form the image of the eye fundus 10a on the focusing screen 26. If the examiner 29 depresses a shutter button, not shown, as is well known after focusing, the image of the eye fundus will be photographed on the film surface 25 after the mirror 24 jumps up.

The optical condition in the eye being examined will now be described in detail by reference to FIG. 3. As can be seen from this figure, the observation opening 22 is conjugate with an imaginarily shown opening 22' and thus, a wide angle of view will be obtained even if the sizes of light-intercepting portions 32a' and 33a' are made into the same sizes as FIG. 1.

On the other hand, the opening 22' conjugate with the observation opening 22 lies at a position whereat the magnification of the reflected image on the rear surface of the crystalline lens (by an optical system determined by the curvature $r_1$ of the rear surface of the crystalline lens, the refractive index n of the crystalline lens and the curvature $r_2$ of the front surface of the crystalline lens) is approximately one-to-one magnification and therefore, according to FIG. 3, it will be seen that the reflected light from a portion A in which the observation optical path and the illumination optical path rearward of the rear surface of the crystalline lens 2 are seen overlapping each other hardly reaches the opening 22'. Accordingly, as compared with the prior art apparatus in which a light-intercepting portion is formed on the rear surface of the crystalline lens and the pupil position is made conjugate with the observation opening, the images of the light-intercepting portions are not formed on the rear surface of the crystalline lens and therefore, it is possible to provide a great quantity of illuminating light even for the same angle of view.

In the case of a standard eye (by the model eye of Gulstrand), the position conjugate with the observation opening is set to a position about 1.4 mm rearward of the vertex of the cornea and about 2.2 mm forward of the front surface of the crystalline lens. That is, this position is the position whereat the magnification of the reflected image on the rear surface of the crystalline lens is approximately one-to-one magnification. Accordingly, as regards the position between the light-intercepting members 32 and 33 optically equivalent to the observation opening 22 relative to the eye 10 being examined, the ratio of spacing of the position equivalent to the light-intercepting member 33 to the position equivalent to the light-intercepting member 32 is 11:7.

I claim:

1. In an eye fundus observation apparatus wherein light-intercepting members for eliminating flare are provided at predetermined positions in an illumination optical path which are substantially conjugate with the cornea and the front surface of the crystalline lens of an eye being examined in a condition in which said apparatus is focused to the fundus of the eye, the improvement comprising:

an observation opening formed at a position substantially conjugate with a position between the cornea and the front surface of the crystalline lens of the eye whereat the magnification of the reflected image on the rear surface of the crystalline lens is approximately one-to-one magnification in a condition in which said apparatus is focused to the fundus of the eye.

2. An ophthalmoscopic optical system including:

objective means which confronts an eye being examined;

an image forming lens means which is arranged on the image side of said objective means;

an illuminating system for illuminating the fundus of the eye, said illuminating system comprising at least one light source, a condenser lens and relay lens means;

reflecting means which is disposed between said objective means and said image forming lens means and which serves to reflect the light emitted from said illuminating system toward said objective means;

a first stop provided in said illuminating system at a position which is substantially conjugate with the cornea of the eye, said first stop being arranged to be large enough so that its image covers the area on the cornea through which light reflected by the fundus of the eye passes;

a second stop provided in said illuminating system at a position which is substantially conjugate with the front surface of the crystalline lens of the eye, said second stop being large enough so that its image covers an area on the front surface of the crystalline lens through which light reflected by the fundus of the eye passes; and an observation opening formed at a position substantially conjugate with a position between the cornea and the front surface of the crystalline lens of the eye whereat the magnification of the reflected image on the rear surface of the crystalline lens is approximately one-to-one magnification (one time).

3. An ophthalmoscopic optical system according to claim 2, wherein said first stop and said second stop are disposed between said condenser lens and said relay lens of said illuminating system in the named order from said condenser lens side.

4. An ophthalmoscopic optical system according to claim 3, wherein the position in the illuminating optical system which is optically equivalent to said observation opening relative to said eye lies between at least said first stop and said second stop, and the ratio of the spacing between said second stop and said position to the spacing between said first stop and said position is 7:11.

5. An ophthalmoscopic optical system according to claim 3 or 4, wherein said first stop and said second stop are black spots provided on a transparent flat plate, said black spots being formed on an illumination optical axis.

6. An ophthalmoscopic optical system according to claim 4, wherein said equivalent position lying between said first stop and said second stop is formed with a conjugate position between said reflecting means and said relay lens by said relay lens, and the position conjugate with said conjugate position by said objective means is coincident with the position conjugate with said observation opening by said objective means.

* * * * *